(12) United States Patent
Blatt et al.

(10) Patent No.: US 6,890,561 B1
(45) Date of Patent: May 10, 2005

(54) MICROENCAPSULATED AND CONTROLLED-RELEASE FORMULATIONS OF ISOFLAVONE FROM ENRICHED FRACTIONS OF SOY AND OTHER PLANTS

(75) Inventors: Yoav Blatt, Rehovot (IL); Oded Arad, Rehovot (IL); Eugene Kimelman, Tel Aviv (IL); David Cohen, Petach Tikva (IL); Rika Pinto, Tel-Aviv (IL); Avner Rotman, Rehovot (IL)

(73) Assignee: Bio Dar Ltd., Yavne (IL)

( * ) Notice: Subject to any disclaimer, the term of this patent is extended or adjusted under 35 U.S.C. 154(b) by 215 days.

(21) Appl. No.: 10/069,388

(22) PCT Filed: Aug. 15, 2000

(86) PCT No.: PCT/IL00/00494

§ 371 (c)(1),
(2), (4) Date: Jun. 28, 2002

(87) PCT Pub. No.: WO01/13890

PCT Pub. Date: Mar. 1, 2001

(30) Foreign Application Priority Data

Aug. 19, 1999 (IL) ................................................. 131508

(51) Int. Cl.⁷ ............................ A61K 9/14; A61K 9/16; A61K 9/20; A61K 9/22; A61K 9/48
(52) U.S. Cl. ....................... 424/490; 424/451; 424/457; 424/458; 424/464; 424/465; 424/468; 424/469; 424/470; 424/489; 424/493; 424/494; 424/495
(58) Field of Search ................................. 424/451, 457, 424/458, 464, 465, 468, 469, 470, 489, 490, 493, 494, 495

(56) References Cited

U.S. PATENT DOCUMENTS

| 4,708,874 | A | | 11/1987 | De Haan et al. ............ 424/470 |
|---|---|---|---|---|
| 5,424,331 | A | * | 6/1995 | Shlyankevich .............. 514/456 |
| 5,506,211 | A | * | 4/1996 | Barnes et al. ................. 514/27 |
| 5,560,928 | A | | 10/1996 | DeFelice ..................... 424/466 |
| 5,707,353 | A | | 1/1998 | Mazer .......................... 604/83 |
| 5,780,060 | A | | 7/1998 | Levy et al. .................. 424/489 |
| 5,847,108 | A | * | 12/1998 | Kanaoka et al. ............ 536/103 |
| 5,985,282 | A | | 11/1999 | Haveson ................... 424/195.1 |
| 6,004,558 | A | * | 12/1999 | Thurn et al. ................. 424/757 |
| 6,117,429 | A | * | 9/2000 | Bucci .......................... 424/729 |
| 6,248,378 | B1 | * | 6/2001 | Ganan-Calvo ............... 426/89 |
| 6,340,478 | B1 | * | 1/2002 | Blatt et al. .................. 424/489 |
| 2003/0175345 | A1 | * | 9/2003 | Hite et al. ................... 424/468 |

FOREIGN PATENT DOCUMENTS

| EP | 0702957 | | 12/1998 | .......... A61K/35/78 |
|---|---|---|---|---|
| EP | 0922450 | | 6/1999 | ............ A61K/9/20 |
| JP | 2000351720 A | * | 12/2000 | ............ A61K/7/32 |
| WO | 00/20017 | | 4/2000 | .......... A61K/35/78 |
| WO | 00/30605 | | 6/2000 | ............ A61K/9/00 |

OTHER PUBLICATIONS

Bauer et al., Coated Pharmaceutical Dosage Forms. Fundamentals, Manufacturing Techniques, Biopharmaceutical Aspects, Test Methods and Row Materials, CRC Press, Washington, D.C. 1998.
Remington's Pharmaceutical Sciences, 8th Edition, Mack Publishing Company, 1990, pp. 1288–1300.
Handbook of Pharmaceutical Excipients, pp. 81–90, 1986, by the American Pharmaceutical Association & Pharmaceutical Society of Great Britain.
USP 24, Test 786, pp. 1969–1970.

* cited by examiner

*Primary Examiner*—Thurman K. Page
*Assistant Examiner*—S. Tran
(74) *Attorney, Agent, or Firm*—Darby & Darby

(57) ABSTRACT

There is provided an orally-administrable formulation for the controlled release or stable storage of a granulated isoflavone-enriched fraction or mixture of such fractions, comprising at least one granulated isoflavone-enriched fraction and at least one carrier, diluent or excipient therefor. Preferably, the formulation is characterized in that the total in vitro dissolution time of said formulation required for release of 75% of the active ingredients available from the formulation is between about 4 and about 18 hours, as determined by the U.S.P. XXIII paddle method at a paddle speed of 75 rpm, using simulated intestinal fluid without the digestive enzymes normally found in intestinal fluid, at pH 6.8, and a temperature of 37° C. A process for the preparation of such a formulation is also provided.

32 Claims, No Drawings

MICROENCAPSULATED AND CONTROLLED-RELEASE FORMULATIONS OF ISOFLAVONE FROM ENRICHED FRACTIONS OF SOY AND OTHER PLANTS

FIELD OF THE INVENTION

The present invention relates to formulations for the controlled or extended release of certain bioactive compounds, and to processes for the preparation of the same.

BACKGROUND OF THE INVENTION

Isoflavones are compounds found in soy and other plants.

In addition to having estrogenic activity, isoflavones also possess other biological properties including:

Strong antioxidant activity

Strong anti cancer activity

Moderate anti-inflammatory activity

It has been established that isoflavone-enriched fractions or extracts of soy or other plants can serve as important nutritional supplements and therapeutic materials. However, it has been found that many of these factions or extracts are unstable and that when stored for long periods, the active ingredients are often eliminated or otherwise rendered inactive. In addition, some, if not all, of the isoflavones contained in these fractions or extracts are quickly eliminated from the body.

SUMMARY OF THE INVENTION

The present invention seeks to provide improved preparations of isoflavone-enriched fractions which preparations offer a convenient oral dosage form for supplying optimum plasma concentrations of the biologically active compounds contained in the fractions (isoflavones such as Deidzein, Genistein, and Glycitain, as well as other materials) and which facilitates user compliance with recommended procedures.

There is thus provided in accordance with a preferred embodiment of the invention an orally-administrable formulation for the controlled release of an isoflavone-enriched fraction or mixture of such fractions, said formulation comprising at least one plant fraction enriched in isoflavones and at least one carrier, diluent or excipient therefor, said formulation being formulated so as to slowly release the isoflavones contained therein.

There is also provided in accordance with a preferred embodiment of the invention an orally-administrable formulation for the stable storage of an isoflavone-enriched fraction or mixture of such fractions, said formulation comprising at least one plant fraction enriched in isoflavones and at least one carrier, diluent or excipient therefor, said formulation being formulated so as to substantially maintain the activity of the isoflavones contained therein for at least six months under storage conditions of standard temperature and pressure.

In the context of the present description and claims, the term "isoflavone-containing fraction" will be understood to refer to an extract or fraction in powdered, granulated or oily form, obtained from soy or other plants, enriched in isoflavones, i.e. containing isoflavones in a higher concentration than is found in an extract from the whole plant. Such fractions may also contain other compounds commonly found in soy or plant fractions or extracts that contain isoflavones, as is known in the art.

In the context of the present description and claims, the term "slowly release" will be understood to mean release the material contained therein into the body over a sustained period, typically about 8–12 hours, although longer periods of time, e.g. 18–24 hours or more, are contemplated within the scope of the invention.

In one preferred embodiment of the invention, the orally-administrable formulation for the controlled release of a granulated isoflavone-enriched fraction comprises at least one granulated isoflavone-enriched fraction and at least one carrier, diluent or excipient therefor, and is characterized in that the total in vitro dissolution time of the formulation required for release of 75% of the active ingredients available from the formulation, is between about 4 and about 18 hours, as determined by the U.S.P. XXIII paddle method at a paddle speed of 75 rpm, using simulated intestinal fluid without the digestive enzymes normally found in intestinal fluid, at pH 6.8, and a temperature of 37° C.

In one preferred embodiment of the invention, the formulation is characterized in that the total amount of granulated isoflavone-enriched fractions contained therein is from about 1 to about 95 wt. %.

In another preferred embodiment of the invention, the formulation is in a form selected from the group consisting of: (i) a matrix tablet, (ii) a multicomponent formulation, (iii) a microcapsule of generally spherical shape, (iv) a microcapsule of generally non-spherical shape, (v) a capsule containing microcapsules, and (vi) a tablet containing microcapsules.

In another preferred embodiment of the invention, the formulation comprises at least one granulated isoflavone-enriched fraction mixed or coated with an excipient or mixture of excipients selected from the group consisting of synthetic polyvinyl-type polymers, synthetic polyethylene-type polymers, cellulose-type polymers, synthetic polyacrylate-type polymers, fats, waxes, sugars and sugar alcohols.

In one preferred embodiment of the invention, the formulation is in the form of a tablet comprising at least one granulated isoflavone-enriched fraction embedded in a mixture of polyvinyl chloride an polyvinyl acetate, and magnesium stearate as a lubricant.

In another preferred embodiment of the invention, the formulation is in the form of a tablet comprising at least one granulated isoflavone-enriched fraction embedded in a mixture of polyvinyl chloride and ethylcellulose, magnesium stearate as lubricant, and a material selected from the group of hydroxypropyl methyl cellulose, sodium carboxymethyl cellulose and paraffin.

In a preferred embodiment of the invention, the formulation is in the form of a hard gelatin two-piece capsule filled with microcapsules containing at least one granulated isoflavone-enriched fraction.

In another preferred embodiment of the invention, the formulation is in the form of a tablet comprising microcapsules.

The invention also comprises a process for the preparation of an orally-administrable formulation for the controlled release of a granulated isoflavone-enriched fraction or mixture of such fractions, said formulation comprising at least one granulated isoflavone-enriched fraction and at least one carrier, diluent or excipient therefor, said process comprising the steps of:

providing at least one granulated isoflavone-enriched fraction; and incorporating said at least one granulated isoflavone-enriched fraction into said at least one carrier, diluent or excipient therefor;

wherein said formulation is characterized in that the total in vitro dissolution time of said formulation required for release of 75% of the active ingredients from said formulation is between about 4 and about 18 hours, as determined by to the U.S.P. XXIII paddle method, using simulated intestinal fluid without the digestive enzymes normally found in intestinal fluid, at pH 6.8, and a temperature of 37° C.

In one preferred embodiment of the invention, the process is characterized in that the at least one granulated isoflavone-enriched fraction is (i) mixed or coated with an excipient or mixture of excipients selected from the group consisting of synthetic polyvinyl-type polymers, synthetic polyethylene-type polymers, cellulose-type polymers, synthetic polyacrylate-type polymers, fats, waxes, sugars and sugar alcohols, and (ii) then compressed into tablets.

In another preferred embodiment of the invention, the process is characterized in that the at least one granulated isoflavone-enriched fraction is (i) mixed or coated with an excipient or mixture of excipients selected from the group consisting of synthetic polyvinyl-type polymers, synthetic polyethylene-type polymers, cellulose-type polymers, synthetic polyacrylate-type polymers, fats, waxes and sugars, (ii) then processed into a form selected from the group of microcapsules and pellets, and (iii) the microcapsules or pellets are filled into hard gelatin capsules.

In a preferred embodiment of the invention, the process is characterized in that the at least one granulated isoflavone-enriched fraction is (i) mixed or coated with an excipient or mixture of excipients selected from the group consisting of synthetic polyvinyl-type polymers, synthetic polyethylene-type polymers, cellulose-type polymers, synthetic polyacrylate-type polymers, fats, waxes and sugars, (ii) then processed into a form selected from the group of microcapsules and pellets, and (iii) said microcapsules or pellets are compressed into tablets.

There is also provided in accordance with a preferred embodiment of the invention an orally-administrable formulation for the controlled release of a granulated isoflavone-enriched fraction or mixture of such fractions, comprising particles of at least one granulated isoflavone-enriched function coated with a film comprising a mixture of at least one water soluble polymer and at least one water insoluble polymer, the at least one water soluble polymer and the at least one water insoluble polymer being present in a ratio that produces a substantially zero order linear release pattern of at least one active ingredient. In one preferred embodiment of the invention, the particles comprise particles which are non-spherically shaped. In another preferred embodiment of the invention, the particles comprise particles which are spherically shaped.

There is also provided in accordance with a preferred embodiment of the invention an orally-administrable formulation for the controlled release of a granulated isoflavone-enriched fraction or mixture of such fractions, comprising particles of at least one granulated isoflavone-enriched fraction coated with an enteric coating comprising a polymer film comprising a polymer which is insoluble at a pH below about 5.5. In a preferred embodiment of the invention, the particles comprise particles which are non-spherically shaped. In another preferred embodiment of the invention, the particles comprise particles which are spherically shaped.

In a preferred embodiment of the invention, the polymer which is comprised in the polymer film is soluble at a pH of about 5.5 or higher. In another preferred embodiment of the invention, the polymer which is comprised in the polymer film is insoluble at a pH below about 5.0.

In one preferred embodiment of the invention, the polymer which is comprised in the polymer film is hydroxypropylmethyl cellulose phthalate. In another preferred embodiment of the invention, the polymer which is comprised in the polymer film is cellulose acetate phthalate.

In a preferred embodiment of the invention, the water insoluble polymer which is comprised in the polymer film is ethyl cellulose.

In another preferred embodiment of the invention, the water soluble polymer which is comprised in the polymer film is hydroxypropylmethyl cellulose (HPMC).

In a preferred embodiment of the invention, the water insoluble polymer which is comprised in the polymer film is ethyl cellulose and the water soluble polymer which is comprised in the polymer film is hydroxypropylmethyl cellulose (HPMC), and the HPMC/ethyl cellulose ratio is substantially from about 0.05 to about 0.40.

In a preferred embodiment of the invention, the total content of granulated isoflavone-enriched fractions is between ab out 1 to 95 wt %.

In accordance with another preferred embodiment of the invention, there is provided a process for producing an orally-administrable formulation for the controlled release of a granulated isoflavone-enriched fraction or mixture of such fractions, comprising coating particles of granulated isoflavone-enriched fraction or fractions with a first inner mixed polymer film comprising ethyl cellulose and hydroxypropylmethyl cellulose (HPMC), wherein the HPMC/ethyl cellulose ratio is substantially from about 0 to about 0.40 by weight, and then coating said particles coated with said first inner polymer film with a second outer polymer film comprising hydroxypropylmethyl cellulose phthalate, wherein the weight ratio of the outer and inner polymer layers is between about 0.2 to about 5.

DETAILED DESCRIPTION OF PREFERRED EMBODIMENTS OF THE INVENTION

The oal controlled release dosage formulations of granulated isoflavone-enriched fractions, in accordance with the invention, include matrix formulations, such as matrix tablets, and multiparticulate formulations such as microcapsules.

In one preferred formulation of the invention, non-spherically, irregularly shaped isoflavone-enriched fraction granulate particles are coated with a film layer comprising a water insoluble polymer, such as ethyl cellulose, and a water soluble polymer such as hydroxypropylmethyl cellulose (HPMC) and plasticizer such as castor oil in an HPMC/ethyl cellulose weight ratio substantially within the range of 0 to 0.4.

The present invention relates to stable, orally administrable, controlled-release dosage forms of granulated isoflavone-enriched fractions, especially in either matrix formulations such as matrix tablets or in multiparticulate formulations like microcapsules put into two piece capsules. This is done in order to obtain a delivery system of isoflavone-enriched fraction-derived molecules which will ensure a steady supply of the active components (isoflavones and other active components, if present) for a sustained period. By either embedding the granulated isoflavone-enriched fractions into a matrix formulation or incorporating them into a microcapsule formulation, or both, in order to control or extend the release of the components of the isoflavone-enriched fractions into the surroundings, the following advantages may be obtained in comparison with conventional release formulations:

- A slower in vivo absorption of isoflavone-enriched fraction-derived active molecules, and hence optimal plasma peak values, which thus reduces the occurrence of undesired effects.
- Prolonged and steady plasma concentrations of isoflavone-enriched fraction-derived active molecules over 12 hours which can help avoid underdosing between dosage intervals.
- A significant increase in the relative extent of bioavailability (amount of active ingredient per gram of isoflavone-enriched fraction ingested) of isoflavone-enriched fraction-derived active molecules, i.e. the therapeutically relevant component, in comparison to standard release formulations.
- Higher tolerability of the active ingredients, i.e., fewer side effects.
- Reduction in the number of daily doses required, which together with the higher tolerability can significantly increase user compliance.
- Stabilization of the highly sensitive isoflavone-enriched fraction-derived active ingredients and thus extended shelf life of the end product.
- Provision of an enteric-coated formulation in those products which are sensitive to the low pH of the stomach and ensuring their release only in the intestine.

Coating and Matrix Materials for Obtaining Controlled Release

Coating and matrix materials which may be used in accordance with the invention are those known in the art for use in controlled-release formulations, such as:

(a) synthetic polymers of the polyvinyl type, e.g. polyvinylchloride, polyvinylacetate and copolymers thereof, polyvinylalcohol, and polyvinylpyrrolidone;

(b) synthetic polymers of the polyethylene type, e.g. polyethylene and polystyrene;

(c) polymers of the acrylic acid or acrylic acid ester type, e.g. methylmethacrylate or copolymers of acrylic monomers;

(d) biopolymers or modified biopolymers, such as cellulose or cellulose derivatives, e.g. ethylcellulose, cellulose acetate phthalate, cellulose acetate, hydroxypropyl cellulose, hydroxypropylmethyl cellulose, methylcellulose, microcrystalline cellulose, Na-carboxymethyl cellulose, as well as, for example, shellac and gelatin;

(e) fats, oils, higher fatty acids and higher alcohols (i.e. acids and alcohols containing alkyl chains of at least 10 carbon atoms), e.g. aluminum monostearate, cetylalcohol, hydrogenated beef tallow, hydrogenated castor oil, 12-hydroxystearl alcohol, glyceryl mono-or dipalmitate, glyceryl mono-, di- or tristearate, myristyl alcohol, stearic acid, stearyl alcohol, and polyethyleneglycols;

(f) waxes, e.g. bees' wax, carnauba wax, Japan wax, paraffin, spermaceti, and synthetic waxes; and (g) sugars and sugar alcohols, e.g. mannitol, sorbitol, sucrose, xylitol, glucose, and maltose.

Depending on the technique used, the polymers mentioned above can be used as coating agents, matrix excipients or pharmaceutical binders. Whether the polymer will function as a matrix excipient or a pharmaceutical binder will be dependent on the amount of polymer in the formulation.

Combinations of the above mentioned polymers, fats and waxes can also be used for microencapsulation purposes as well as for matrix formation, viz. different polymers can be mixed, a polymer can be mixed with a fat or wax, and so forth.

The encapsulation of the isoflavone-enriched fraction can be achieved in the form of microcapsules, but the encapsulation is not restricted to the micro size, i.e. the range of 50 micrometers to 2000 micrometers, and can be accomplished on larger particles or granules. Throughout the present description and claims, the size of microscopic particles will be understood as referring to size as determined by analytical sieving, as described in USP 24, test 786 at pp. 1969–1970.

The multiparticulate dosage forms, i.e., microcapsules or coated pellets as well as the matrix tablets useful for the present invention can be prepared by any of several known production processes, including conventional granulation and tableting of matrix tablets, pan coating, prilling, extrusion and spheronization, fluid bed processes, spray drying, spray chilling, coacervation and other processes.

Microcapsules or Coated Pellets

Microcapsules or coated pellets micropellets are defined as a solid or liquid core enclosed in a coating. The coating may also be referred to as the wall or shell. As is known in the art, various types of microcapsule structures can be obtained depending on the manufacturing process, e.g. mononuclear spherical, multinuclear spherical, multinuclear irregular, encapsulated mononuclear capsules, dual-walled microcapsules, etc. Where no distinct coating and core region can be observed, the analogous terms are microparticles, microspheres, micromatrices and microbeads. The microcapsules or pellets of the present invention usually have a particle size between about 1 and about 2000 microns.

The microcapsules or coated pellets of granulated isoflavone-enriched fractions can be filled into empty hard gelatin capsules to an extent corresponding to the desired dose, or they can be gently compressed into a tablet by using suitable tablet excipients.

Coated particles of isoflavone-enriched fraction may also be mixed with a pharmaceutical binder to form micropellets, which are then compressed into tablets.

The orally administrable formulations of the invention may comprise micropellets, which are then coated with a pharmaceutically acceptable coating excipient prior to being compressed into tablets. The micropellets can also be filled into capsules.

The formulations of the invention may also comprise microspheres which are then coated with a pharmaceutically acceptable coating excipient prior to being filled into capsules.

Matrix Formulations

Matrix formulations are defined as a drug or other active ingredient embedded in insoluble excipients in order to achieve release by a continuous leaching of the drug from the inert matrix core. The release mechanisms often follows the square root law of Higuchi. This term also applies to a matrix built of hydrophilic substances which in contact with water form a gel of high viscosity.

One type of matrix formulation is a matrix tablet, which is a matrix formulation in tablet form. Such tablets may be coated with an enteric coating, which inhibits or prevents dissolution of the tablets at low pH (below about pH 5, preferably below about pH 5.5), such as is found in the stomach, and enables dissolution of the tablets at higher pH's (e.g. around pH 6.8, such as is found in the intestine).

In accordance with the present invention, capsule forms can be of the ordinary hard-shelled gelatin type containing, for example, surfactants, lubricants, and inert fillers, such as lactose, sucrose, calcium phosphate, or corn starch. For example, the formulations may be presented as hard gelatin capsules wherein the microcapsules of isoflavone enriched fraction are mixed with an inert solid diluent, for example calcium carbonate, calcium phosphate or kaolin. Tablet forms can include as excipients, diluents or carriers excipients, diluents and carriers known in the art, e.g. polymers, resins, plasticizers, fillers, lubricants, solvents, co-solvents, buffer systems, surfactants, preservatives, sweetening agents, flavoring agents, pharmaceutical grade dyes or pigments, and viscosity agents. Particular examples of excipients, diluents or carriers useful in the practice of the present invention include but are not limited to one or more of lactose, sucrose, mannitol, calcium carbonate, sodium carbonate, calcium phosphate or sodium phosphate, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients, as are well known in the art. In accordance with the present invention, the material used to microencapsulate the isoflavone-containing extracts may also function as an excipient, diluent or carrier.

The term "oral dosage form" or "orally adminstrable formulation" as used herein means any formulation intended to be administered to the gastrointestinal tract of an individual via the mouth of said individual, and for purposes of the present invention, the delivered form may be in the form of a tablet, optionally enteric-coated, containing one or more isoflavone-enriched fractions which are preferably microencapsulated, or a capsule, (enteric-coated or non-coated), containing microencapsulated isoflavone-enriched fractions.

"Enteric-coated oral dosage form" as used herein relates to an oral dosage form containing a formulation as described herein which utilizes an enteric coating to effect the release of the isoflavone enriched fractions in the small or large intestine. The enteric coated oral dosage from may be a compressed tablet (coated or uncoated) containing isoflavone enriched fractions, which themselves are preferably microencapsulated, preferably with an enteric coating. The enteric coated oral dosage form may be a gelatin capsule (coated or uncoated) containing microencapsulated isoflavone enriched fractions, preferably wherein the microencapsulation coating is itself an enteric coating. Enteric coated compositions are described by Bauer et al., Coated Pharmaceutical Dosage Forms. Fundamentals, Manufacturing Techniques, Biopharmaceutical Aspects, Test Methods and Raw Materials, CRC Press, Washington, D.C., 1998, the entire contents of which are hereby incorporated by reference.

The term "delayed-release" as used herein refers to a delivery of isoflavone enriched fractions which is effected by formulating the active ingredient in a formulation so that the release will be accomplished at some generally predictable location in the lower intestinal tract more distal to that which would have been accomplished if there had been no alteration in the delivery of the active ingredient. The preferred method for effecting the delayed-release of the active ingredient involves coating (or otherwise encapsulating) said active ingredient with a substance which is not absorbed, or otherwise broken down, by the gastrointestinal fluids to release said active ingredient until a specific desired point in the intestinal tract is reached. A preferred type of delayed-release formulation for use herein is achieved by coating the tablet, capsule, or particles, granules, or beads of active ingredient with a substance which is pH-dependent, i.e., broken down at a pH which is generally present in the small intestine, but not broken down at a pH which is generally present in the stomach. However, if it is desired to effect the topical delivery via the oral administration of a formulation containing the isoflavone enriched fraction to only the large intestine, or to the entire length of the intestinal tract beginning with the small intestine, then the selection of the coating material and/or the method of coating or otherwise combining the isoflavone enriched fraction with the selected coating material or other pharmaceutically-acceptable excipients may be varied or altered as is described herein or by any method known to one skilled in the art. For example, a time delay material such as glyceryl monostearate or glyceryl tristearate alone or with a wax may be employed.

The term "sustained-release" or "controlled release" as used herein means the type of release mechanism designed to effect the delivery of the isoflavone enriched fraction over an extended period of time, as contrasted to the delivery of a delayed-release type dose. The most preferred sustained-release type method for use herein involves the coating of granules of the isoflavone enriched fraction with a pH-independent coating, chosen from the group including, but not limited to ethylcellulose, hydroxypropylmethylcellulose, hydroxypropylcellulose, methylcellulose, hydroxymethylcellulose, hydroxyethylcellulose, and sodium carboxymethylcellulose. Various sustained-release dosage forms may readily be fashioned by one skilled in the art which may achieve the delivery of the isoflavone enriched fraction to both the small intestine and the large intestine, to only the small intestine, or to only the large intestine, depending upon the choice of the various coating materials, and/or coating thickness.

Besides the above mentioned variations in order to obtain the desired release pattern, the excipients may also be varied, as long as they do not affect the activity of the particular isoflavone enriched fraction selected.

As stated hereinabove, pharmaceutically-acceptable excipients include, but are not limited to, polymers, resins, plasticizers, fillers, lubricants, solvents, cosolvents, surfactants, preservatives, sweetener agents, flavoring agents, buffer systems, pharmaceutical-grade dyes or pigments, and viscosity agents.

Flavoring agents among those useful herein include those described in Remington's Pharmaceutical Sciences, 18th Edition, Mack Publishing Company, 1990, pp. 1288–1300, incorporated by reference herein. Dyes or pigments among those useful herein include those described in Handbook of Pharmaceutical Excipients, pp. 81–90, 1986 by the American Pharmaceutical Association & the Pharmaceutical Society of Great Britain, incorporated by reference herein.

To achieve sustained release effect, the microcapsules containing isoflavone enriched faction are preferably formed with coats of one or more polymers, preferably a blend of polymers, at least two of which have different levels of hydrophilicity. Generally, one polymer is more hydrophilic than the other. More hydrophilic polymer coatings generally produce dosage forms which dissolve faster. Conversely, less hydrophilic polymers give coatings which dissolve relatively slowly.

In a preferred embodiment of the invention, the more hydrophilic polymer is polyvinylpyrolidone (PVP), a hydroxypropylcellulose polymer, or a similar polymer. PVPK-30, manufactured by BASF Corporation, and Klucel EF, manufactured by Aqualon, are suitable. Mixtures of the foregoing are also within the scope of the invention.

The less hydrophilic polymer component is typically a cellulosic polymer. Useful cellulosic polymer ingredients include one or more polymers selected from ethyl cellulose, polymethyl(meth)acrylate and the like, as well as mixtures thereof. In this regard, Ethocel available from Dow Corporation is desirable.

The blend of polymers will typically be one in which the ratio of the less-hydrophilic polymer to the more hydrophilic polymer is from about 90:10 to about 50:50. Using ethyl cellulose (EC) polymer and PVP as examples, a suitable EC:PVP ratio will be about 90:10 to about 50:50, with about 80:20 being highly effective.

The coating is typically applied to the isoflavone enriched fractions at a level of about 5 to 45% by weight of the isoflavone enriched fraction component, with coating levels on the order of about 10 to 25 weight percent being typical. Those skilled in the art may of course vary the aforesaid percentages according to their particular needs. Coating is generally effected using apparatus known in the art, for example, a fluidized bed, using known techniques such as the Wurster coating process. Coating generally takes place at about 25–50 degrees Celsius.

While the use of multiple coatings is contemplated, the isoflavone enriched fractions are generally coated once.

Solvents may be utilized in the coating process, and are generally selected from water, acetone, isopropyl alcohol and the like. About 0 to 20% of one or more plasticizers such as, for example, dibutyl sebacate, triethyl citrate and the like can also be used. Anti-tacking agents to prevent agglomeration of coated particles in amounts of about 0 to 50% are also within the scope of the invention. Typical anti-tacking agents include talc, colloidal, silica, magnesium stearate and the like.

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

What is claimed is:

1. An orally-administrable formulation for the controlled release of an isoflavone-enriched fraction or mixture of such fractions, said formulation comprising microcapsules containing at least one granulated plant fraction enriched in isoflavones and at least one carrier, diluent or excipient therefor, said formulation being formulated so as to slowly release the isoflavones contained therein by virtue of said microcapsules being formed with a coating comprising a blend of at least two polymers, at least one of said at least two polymers being more hydrophilic than the other of said at least two polymers, the ratio of the less hydrophilic polymer to said more hydrophilic polymer being from about 90:10 to 50:50, said coating being applied to said granulated isoflavone-enriched fraction at a level of about 5 to about 45% by weight of said granulated isoflavone-enriched fraction component.

2. An orally-administrable formulation for the stable storage of an isoflavone-enriched fraction or mixture of such fractions, said formulation comprising microcapsules containing at least one granulated plant fraction enriched in isoflavones and at least one carrier, diluent or excipient therefor, said formulation being formulated so as to substantially maintain the activity of the isoflavones contained therein for at least six months under storage conditions of standard temperature and pressure by virtue of said microcapsules being formed with a coating comprising a blend of at least two polymers, at least one of said at least two polymers being more hydrophilic than the other of said at least two polymers, the ratio of the less hydrophilic polymer to said more hydrophilic polymer being from about 90:10 to 50:50, said coating being applied to said granulated isoflavone-enriched fraction at a level of about 5 to about 45% by weight of the granulated isoflavone-enriched fraction component.

3. An orally-administrable formulation for the controlled release of a granulated isoflavone-enriched fraction or mixture of such fractions according to claim 1, comprising at least one granulated isoflavone-enriched fraction and at least one carrier, diluent or excipient therefor, characterized in that the total in vitro dissolution time of said formulation required for release of 75% of the active ingredients available from said formulation is between about 4 and about 18 hours, as determined by the U.S.P. XXIII paddle method at a paddle speed of 75 rpm, using simulated intestinal fluid without the digestive enzymes normally found in intestinal fluid, at pH 6.8, and a temperature of 37° C.

4. A formulation according to claim 3 characterized in that the total amount of granulated isoflavone-enriched fractions contained therein is from about 1 to about 95 wt. %.

5. A formulation according to claim 3, wherein said formulation is in a form selected from the group consisting of: (i) a matrix tablet, (ii) a multicomponent formulation, (iii) a microcapsule of generally spherical shape, (iv) a microcapsule of generally non-spherical shape, (v) a capsule containing microcapsules, and (vi) a tablet containing microcapsules.

6. A formulation according to claim 3 comprising at least one granulated isoflavone-enriched fraction mixed or coated with an excipient or mixture of excipients selected from the group consisting of synthetic polyvinyl-type polymers, synthetic polyethylene-type polymers, cellulose-type polymers, synthetic polyacrylate-type polymers, fats, waxes, sugars and sugar alcohols.

7. A formulation according to claim 3 in the form of a tablet comprising: at least one granulated isoflavone-enriched fraction embedded in a mixture of polyvinyl chloride and polyvinyl acetate; and magnesium stearate as a lubricant.

8. A formulation according to claim 3 in the form of a tablet comprising: at least one granulated isoflavone-enriched fraction embedded in a mixture of polyvinyl chloride and ethyl cellulose; magnesium stearate as lubricant; and a material selected from hydroxypropyl methyl cellulose, sodium carboxymethyl cellulose and paraffin.

9. A formulation according to claim 3 in the form of a hard gelatin two-piece capsule filled with microcapsules containing at least one granulated isoflavone-enriched fraction.

10. A formulation according to claim 3 in the form of a tablet comprising microcapsules.

11. A process for the preparation of an orally-administrable formulation for the controlled release of granulated isoflavone-enriched fraction or mixture of such fractions, said formulation comprising at least one granulated isoflavone-enriched fraction, said process comprising the steps of:

providing at least one granulated isoflavone-enriched fraction, forming microcapsules by coating granules of said at least one granulated isoflavone enriched fraction with a coating comprising a blend of at least two polymers, at least one of said at least two polymers being more hydrophilic than the other of said at least two polymer, the ratio of the less hydrophilic polymer to said more hydrophilic polymer being from about 90:10 to 50:50, said coating being applied to said isoflavone-enriched fraction at a level of about 5 to about 45% by weight of the isoflavone-enriched fraction component; and incorporating said microcapsules into said formulation, wherein said formulation is characterized in that the total in vitro dissolution of said formulation required for release of 75% of the active ingredients from said formulation based upon the total amount of active ingredients present in said formulation is between about 4 and about 18 hours, as determined by the USP XXIII paddle method at a paddle speed of 75 rpm, using simulated intestinal fluid without the digestive enzymes normally found in intestinal fluid, at pH 6.8 and a temperature of 37° C.

12. The process according to claim 11 characterized in that said at least one granulated isoflavone-enriched fraction is (i) coated with a blend of at least two polymers selected from the group consisting of synthetic polyvinyl-type polymers, synthetic polyethylene-type polymers, cellulose-type polymers, synthetic polyacrylate-type polymers, fats, waxes, sugars and sugar alcohols, and (ii) then compressed into tablets compressed into tablets.

13. The process according to claim 11 characterized in that said microcapsules are filled into hard gelatin capsules.

14. The process according to claim 11 characterized in that said microcapsules are compressed into tablets.

15. An orally-administrable formulation for the controlled release of a granulated isoflavone-enriched fraction or mixture of such fractions comprising particles of at least one granulated isoflavone-enriched fraction coated with a film comprising a mixture of at least one water soluble polymer and at least one water insoluble polymer, said at least one water soluble polymer and at least one water insoluble polymer being present in a ratio of between about 10:90 and 50:50 and at a level of about 5 to 45% by weight of the granulated isoflavone enriched fraction, that produces a substantially zero order linear release pattern of at least one active ingredient.

16. An orally-administrable formulation according to claim 15, wherein said particles comprise particles which are non-spherically shaped.

17. An orally-administrable formulation according to claim 15, wherein said particles comprise particles which are spherically shaped.

18. An orally-administrable formulation according to claim 15, wherein said at least one active ingredient is Deidzein.

19. An orally-administrable formulation according to claim 15, wherein said at least one active ingredient is Genisein.

20. An orally-administrable formulation according to claim 15, wherein said at least one active ingredient is an Glycitain.

21. An orally-administrable formulation for the controlled release of a granulated isoflavone-enriched fraction or mixture of such fractions, comprising particles of at least one granulated isoflavone-enriched fraction coated with an enteric coating comprising a polymer film comprising a blend of at least two polymers which is insoluble at a pH below about 5.5, at least one of said at least two polymers being more hydrophilic than the other of said at least two polymers, the ratio of the less hydrophilic polymer to said more hydrophilic polymer being from about 90:10 to 50:50, said coating being applied to said granulated isoflavone-enriched fraction at a level of about 5 to about 45% by weight of the isoflavone-enriched fraction component.

22. An orally-administrable formulation according to claim 21, wherein said particles comprise particles which are non-spherically shaped.

23. An orally-administrable formulation according to claim 21, wherein said particles comprise particles which are spherically shaped.

24. A formulation according to claim 21, wherein said polymer is soluble at a pH of about 5.5 or higher.

25. A formulation according to claim 21, wherein said polymer is insoluble at a pH below about 5.0.

26. A formulation according to claim 21, wherein said polymer is hydroxypropylmethyl cellulose phthalate.

27. A formulation according to claim 21, wherein said polymer is cellulose acetate phthalate.

28. A formulation according to claim 15 wherein said water insoluble polymer is ethyl cellulose.

29. A formulation according to claim 15 wherein said water soluble polymer is hydroxypropylmethyl cellulose (HPMC).

30. A formulation according to claim 15 wherein said water insoluble polymer is ethyl cellulose and said water soluble polymer is hydroxypropylmethyl cellulose (HPMC), and wherein the HPMC/ethyl cellulose ratio is substantially from about 0.05 to about 0.40.

31. A formulation according to claim 15 wherein the total content of granulated isoflavone-enriched fractions is between about 1 to 95 wt. %.

32. A process for producing an orally-administrable formulation for the controlled release of a granulated isoflavone-enriched fraction or mixture of such fractions, comprising coating particles of at least one granulated isoflavone-enriched fraction with an inner, mixed polymer film comprising ethyl cellulose and hydroxypropylmethyl cellulose (HPMC), wherein the HPMC/ethyl cellulose ratio is substantially from about 0 to about 0.04 by weight, and then coating said particles coated with said inner polymer film with an outer polymer film comprising hydroxypropylmethyl cellulose phthalate, wherein the weight ratio of the outer to inner polymer layers is between 0.2 to 3.0, and wherein said coating is applied at a level of about 5 to 45% by weight of said granulated isoflavone enriched fraction.

* * * * *